(12) United States Patent
McKinney et al.

(10) Patent No.: US 9,579,503 B2
(45) Date of Patent: Feb. 28, 2017

(54) INTERFACE MODULE ALLOWING DELIVERY OF TISSUE STIMULATION AND ELECTROSURGERY THROUGH A COMMON SURGICAL INSTRUMENT

(75) Inventors: Jeremy Michael McKinney, Jacksonville, FL (US); Wenjeng Li, Saint Johns, FL (US); Kevin Lee McFarlin, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1231 days.

(21) Appl. No.: 13/253,354

(22) Filed: Oct. 5, 2011

(65) Prior Publication Data

US 2013/0090641 A1    Apr. 11, 2013

(51) Int. Cl.
| | |
|---|---|
| *A61B 18/18* | (2006.01) |
| *A61N 1/36* | (2006.01) |
| *A61B 5/00* | (2006.01) |
| *A61B 18/12* | (2006.01) |
| *A61B 18/14* | (2006.01) |
| *A61B 18/00* | (2006.01) |

(52) U.S. Cl.
CPC ............. *A61N 1/36* (2013.01); *A61B 5/4893* (2013.01); *A61B 18/1206* (2013.01); *A61B 18/1445* (2013.01); *A61B 18/1477* (2013.01); *A61B 2018/0063* (2013.01); *A61B 2018/00589* (2013.01); *A61B 2018/00601* (2013.01); *A61B 2018/124* (2013.01)

(58) Field of Classification Search
CPC ...... A61B 18/1206; A61B 2018/00589; A61B 2018/00601; A61B 2018/124; A61B 5/4893; A61N 1/36

USPC .......................................................... 606/34
See application file for complete search history.

(56) References Cited

U.S. PATENT DOCUMENTS

| 5,971,983 A | 10/1999 | Lesh | |
|---|---|---|---|
| 2002/0105336 A1* | 8/2002 | Swale | .......................... 324/508 |

(Continued)

FOREIGN PATENT DOCUMENTS

| CN | 1227476 A | 9/1999 |
|---|---|---|
| CN | 1181790 C | 12/2004 |

(Continued)

OTHER PUBLICATIONS

Notification of Transmittal of the International Search Report and the Written Opinion of the International Searching Authority, or the Declaration (PCT/US2012/058984) dated Apr. 17, 2014 (9 pages).

(Continued)

*Primary Examiner* — Christopher D Koharski
*Assistant Examiner* — Pamela M Bays
(74) *Attorney, Agent, or Firm* — Dicke, Billig & Czaja, PLLC

(57) ABSTRACT

Concepts presented herein relate to an interface module that can be electrically coupled to an electrical stimulation generator, a radio frequency generator and an instrument. A selection module is coupled to the interface module and operates in a first mode to deliver electrical stimulation signals from the electrical stimulation generator to the instrument and in a second mode to deliver radio frequency signals from the radio frequency generator to the instrument.

13 Claims, 3 Drawing Sheets

(56) References Cited

U.S. PATENT DOCUMENTS

| | | |
|---|---|---|
| 2004/0167585 A1* | 8/2004 | Kovak .................... A61N 1/32 607/48 |
| 2004/0172011 A1 | 9/2004 | Wang et al. |
| 2007/0156127 A1* | 7/2007 | Rioux et al. .................... 606/32 |
| 2008/0114350 A1* | 5/2008 | Park .................. A61B 18/1206 606/34 |
| 2008/0183169 A1* | 7/2008 | Klimovitch et al. ........... 606/42 |
| 2008/0221565 A1* | 9/2008 | Eder et al. ..................... 606/40 |
| 2010/0198099 A1 | 8/2010 | Murphy et al. |
| 2011/0034826 A1 | 2/2011 | Notz et al. |
| 2011/0270120 A1 | 11/2011 | McFarlin et al. |

FOREIGN PATENT DOCUMENTS

| | | |
|---|---|---|
| JP | S6080446 A | 5/1985 |
| WO | 00/13600 A1 | 3/2000 |
| WO | 0112089 A1 | 2/2001 |
| WO | 03/034931 A1 | 5/2003 |
| WO | 2006/123398 A1 | 11/2006 |
| WO | 2008/014465 A2 | 1/2008 |
| WO | 2011136962 A1 | 11/2011 |

OTHER PUBLICATIONS

Notification of Transmittal of the International Search Report and the Written Opinion of the International Searching Authority, or the Declaration (PCT/US2012/058984) dated Jan. 9, 2013 (13 pages).

* cited by examiner

INTERFACE MODULE ALLOWING DELIVERY OF TISSUE STIMULATION AND ELECTROSURGERY THROUGH A COMMON SURGICAL INSTRUMENT

BACKGROUND

Evoked potential (EP) monitoring assists a surgeon in locating nerves within an obscured surgical field, as well as preserving and assessing nerve function in real-time during surgery. To this end, evoked potential monitoring is commonly employed to capture responses resulting from stimulation of the tissue of interest (e.g., direct nerve, muscle, etc.). Evaluating the aforementioned EP responses allows for immediate assessment of the integrity of the electrical signal path through the tissue of interest. Electrical stimulation can cause excitement of the tissue. During electrical stimulation, a surgical probe applies a stimulus signal near the area where the subject tissue may be located. If the stimulation probe contacts or is reasonably near the tissue, the applied stimulus signal is transmitted to the tissue evoking a response. Excitation of the tissue generates an electrical impulse that is sensed by the recording electrodes (or other sensing device). The recording electrode(s) signal the sensed electrical impulse information to the surgeon for interpretation in the context of determining (EP) activity. For example, the EP activity can be displayed on a monitor and/or presented audibly.

Evoked potential monitoring is useful for a multitude of different surgical procedures or evaluations that involve or relate to nerve conduction. Evaluation of these nerves can assist in preservation of the intended electrophysical function during procedures where there exists a high probability of damage to these tissues. For example, various head and neck surgical procedures (e.g., parotidectomy and thyroidectomy) require locating and identifying cranial and peripheral motor nerves. In some instances, an electrosurgical unit is used during these surgical procedures. Current electrosurgical units include a conductive tip or needle that serves as one electrode in an electrical circuit which is completed via a grounding electrode coupled to the patient. Incision of tissue is accomplished by applying a source of electrical energy (most commonly, a radio-frequency generator) to the tip. Upon application of the tip to the tissue, a voltage gradient is created, thereby inducing current flow and related heat generation at the point of contact. With sufficiently high levels of electrical energy, the delivered energy is sufficient to cut the tissue and, advantageously, to simultaneously cauterize severed blood vessels.

Due to the levels of electrical energy generated by electrosurgical units, systems for evoked potential monitoring experience a large amount of electrical interference when used during electrosurgical procedures. The electrical interference can create a condition where signal levels are obscured. For example, during EP monitoring, electrosurgical activity can create artifacts (e.g., false positives) as well as introduce a significant amount of noise in the evoked potential monitoring system. As a result, current techniques involve using a probe to mute all channels of the evoked potential monitoring system during an electrosurgical procedure. Thus, monitoring of EP activity is typically suspended during operation of the electrosurgical unit. In order for a surgeon to prevent cutting a nerve with the electrosurgical unit, the surgeon will cut for a brief period and then stop cutting such that evoked potential monitoring can be restored. If no EP activity is detected, the surgeon can then cut for another brief period, while pausing intermittently to restore evoked potential monitoring so as to prevent from cutting a nerve. This process is repeated until the surgeon has completed the electrosurgical procedure. Without being able to monitor EP activity, there exists a higher probability of resulting impaired electrophysical function.

SUMMARY

Concepts presented herein relate to an interface module that can be electrically coupled to an electrical stimulation generator, a radio frequency generator, and an instrument. A selection module is coupled to the interface module and operates in a first mode to indicate and control delivery of electrical stimulus signals from the electrical stimulation generator to the instrument and in a second mode to indicate and control delivery of radio frequency signals from the radio frequency generator to the instrument. The interface module includes a plurality of relays and a controller to selectively deliver desired signals to the instrument.

DETAILED DESCRIPTION

Figure 1:
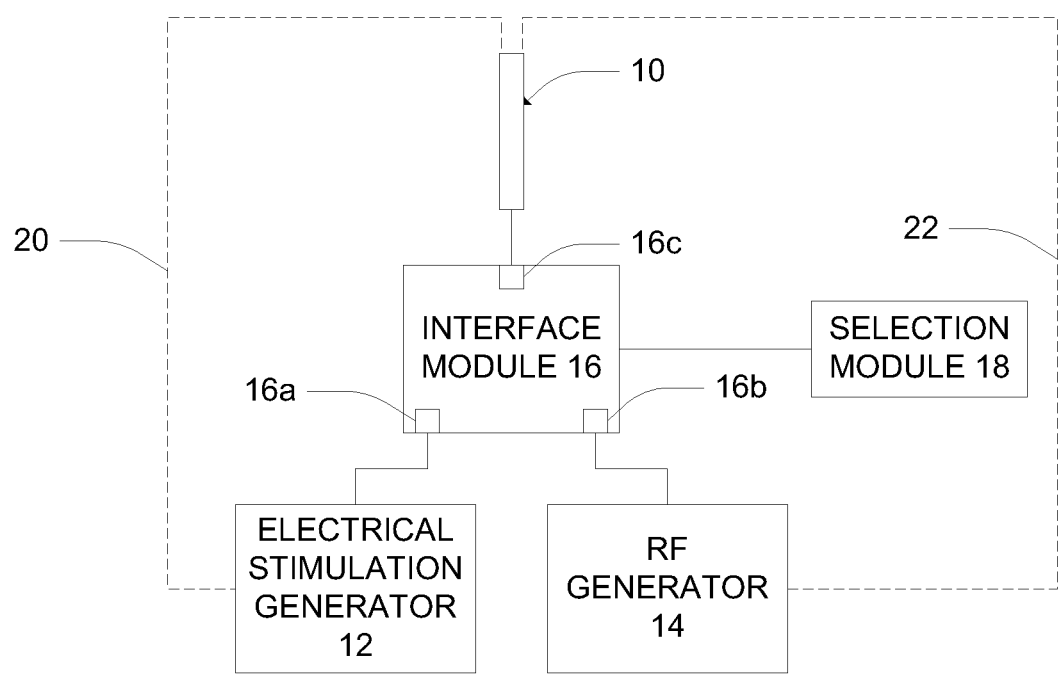
FIG. 1 is a schematic block diagram of components selectively delivering signals to an instrument.

FIG. 1 is a schematic block diagram of an instrument 10 for selectively applying signals received from an electrical stimulation generator 12 and a radio frequency (RF) generator 14 to tissue of interest in a surgical procedure. An interface module 16 is electrically coupled to the stimulation generator 12 and the RF generator 14 to selectively operate in a plurality of modes to deliver a desired output to the instrument 10. In particular, interface module 16 includes a first input 16a electrically coupled to the electrical stimulation generator 12, a second input 16b electrically coupled to RF generator 14 and an output 16c electrically coupled to instrument 10.

A selection module (e.g., a switch or network) 18 is coupled to interface module 16 and operates to provide an indication of mode, and to selectively deliver electrical stimulation signals or RF signals provided by electrical stimulation generator 12 and RF generator 14, respectively, to instrument 10. In particular, selection module 18 is configured to complete either a first, electrical stimulation circuit 20 or a second, RF circuit 22. As such, when instrument 10 is brought into contact with tissue of a patient and electrical stimulation circuit 20 is complete, electrical stimulation signals from electrical stimulation generator 12 are delivered to the tissue. Alternatively, when RF circuit 22 is complete, radio frequency signals from RF generator 14 are delivered to the tissue.

Instrument 10 can be any instrument that electrically interfaces with a patient to perform nerve monitoring and/or electrosurgery. In one embodiment, instrument 10 can be a bipolar forceps, a laparoscopic bipolar instrument or a monopolar cautery pencil. Instrument 10 can also include any nerve stimulating probe capable of meeting the electrical requirements defined for electrosurgical tools.

In one embodiment, electrical stimulation generator 12 is part of a NIM-Response® 3.0 nerve monitoring system available from Medtronic Xomed, Inc. of Jacksonville, Fla., and configured to deliver electrical stimulation signals to instrument 10 so as to excite tissue in contact with instrument 10. In another embodiment, the electrical stimulation signals provided by electrical stimulation generator 12 are of sufficient strength so as to stimulate associated tissue yet inherently safe so as to prevent physical trauma to the associated tissue. In this instance, the electrical stimulation generator 12 operates with relatively low voltage levels (e.g., in the range of +/−0-100 millivolts) when compared to voltage levels of RF generator 14.

In one embodiment, RF generator 14 can be part of an electrosurgical unit (ESU) configured to manipulate tissue, for example through cutting, cauterizing and hemostasis. Example ESUs are available through Valleylab of Boulder, Colo.; ERBE of Marietta, Ga.; ConMed Corporation of Utica, N.Y.; Gyms ACMI of Southborough; Mass. and Megadyne of Draper, Utah. RF generator 14 can be configured to achieve various different tissue effects, as desired. In one embodiment, RF generator 14 is configured to deliver signals at electrocautery frequencies at various voltage levels. For example, the RF generator can operate at voltage levels greater than +/−200 volts.

Interface module 16 integrates electrical stimulation generator 12 and RF generator 14. To this end, interface module 16 can be equipped to receive cabling from electrical stimulation generator 12, RF generator 14 and instrument 10. Interface module 16 can further be equipped to receive input from and/or provide output to other devices as desired.

Selection module 18 can take many forms including a manual switch, electrical switch or electrical network capable of automatically delivering signals from electrical stimulation generator 12 and RF generator 14. The selection module 18 can be directly integrated within interface module 16 or positioned remotely. In one embodiment, selection module 18 can be a mechanical switch directly integrated into instrument 10 so that a user can easily select what signals are sent to instrument 10 while operating instrument 10. Example mechanical switches include dome switches, rocker switches, toggle switches, etc. For example, instrument 10 may include a handle with selection module 18 maintained within the handle. In this embodiment, two way communication is provided between instrument 10 and interface module 16 so that selection module 18 notifies interface module 16 of a desired signal to be sent to instrument 10. In a further embodiment, selection module 18 can be a foot pedal operable by a surgeon, wherein the interface module 16 is configured to deliver electrical signals from the electrical stimulation generator 12 when the foot pedal is not depressed (i.e., a default mode).

In a still further embodiment, selection module 18 can be an automatic electrical switch. The electrical switch can be configured to interleave signals to instrument 10 so as to deliver signals from electrical stimulation generator 12 and RF generator 14 exclusively. In still a further embodiment, selection module 18 can be formed of a combination of mechanical and electrical switches. For example, an electrical switch can continuously interleave electrical stimulation signals into output signals that are sent to instrument 10 while a mechanical switch determines whether signals from RF generator 14 are sent to instrument 10. In yet a further embodiment, selection module 18 can be an electrical network configured to select a signal that is delivered to instrument 10, for example as a function of a frequency of the signal or alternatively combine electrical stimulation signals and RF signals into an output signal.

In a further embodiment, interface module 16 can be capable of two, three or more modes of operation. For example, RF generator 14 can provide multiple distinct operational signals when used as an electrosurgical unit. In one particular embodiment, these RF generator signals are configured for both cutting and coagulation. In this instance, interface module 16 can be configured to operate in three separate modes, namely an electrical stimulation mode, (thus delivering stimulation signals from electrical stimulation generator 12) an RF cutting mode (thus delivering cutting signals from RF generator 14) and an RF coagulation mode (thus delivering coagulation signals from RF generator 14).

In still further embodiments, interface module 16 can include a default mode of operation. For example, interface module 16 can be configured to deliver signals from electrical stimulation generator 12 when a user has not actively selected a desired mode of operation. As discussed above, signals from electrical stimulation generator 12 operates in an inherently safe mode that does not provide physical trauma to tissue in contact with instrument 10. By utilizing a default mode for delivering electrical stimulation, accidental delivery of RF signals to instrument 10 can be prevented. In an alternative default mode, interface module 16 prevents any signals from being transmitted to instrument 10.

Selection module 18 operates to selectively complete electrical stimulation circuit 20 or RF circuit 22. To this end, circuits 20 and 22 can be configured for different modalities, such as monopolar, bipolar and/or combinations thereof. When circuit 20 is complete, current passes from electrical stimulation generator 12, through interface module 16 and to instrument 10, in contact with tissue. Current then passes through tissue from the point of contact with instrument 10 to the point of coupling to the one or more recording electrodes. Current then passes from the recording electrodes back to electrical stimulation generator 12.

In an alternative embodiment, instrument 10 may be a bipolar instrument that includes two electrodes, one serving as an active electrode and one serving as a return electrode. In this case, current flows from electrical stimulation generator 12, through the interface module 16 and to the active electrode of instrument 10. Current then passes through the tissue from the point of contact with the active electrode to the point of contact with the return electrode and back through the return electrode, instrument 10, interface module 16 and to electrical stimulation generator 12. Similarly, RF circuit 22 can include a dispersive pad coupled to tissue in a monopolar configuration and/or instrument 10 can include multiple electrodes in a bipolar configuration so as to complete circuit 22 through tissue of the patient.

Figure 2:
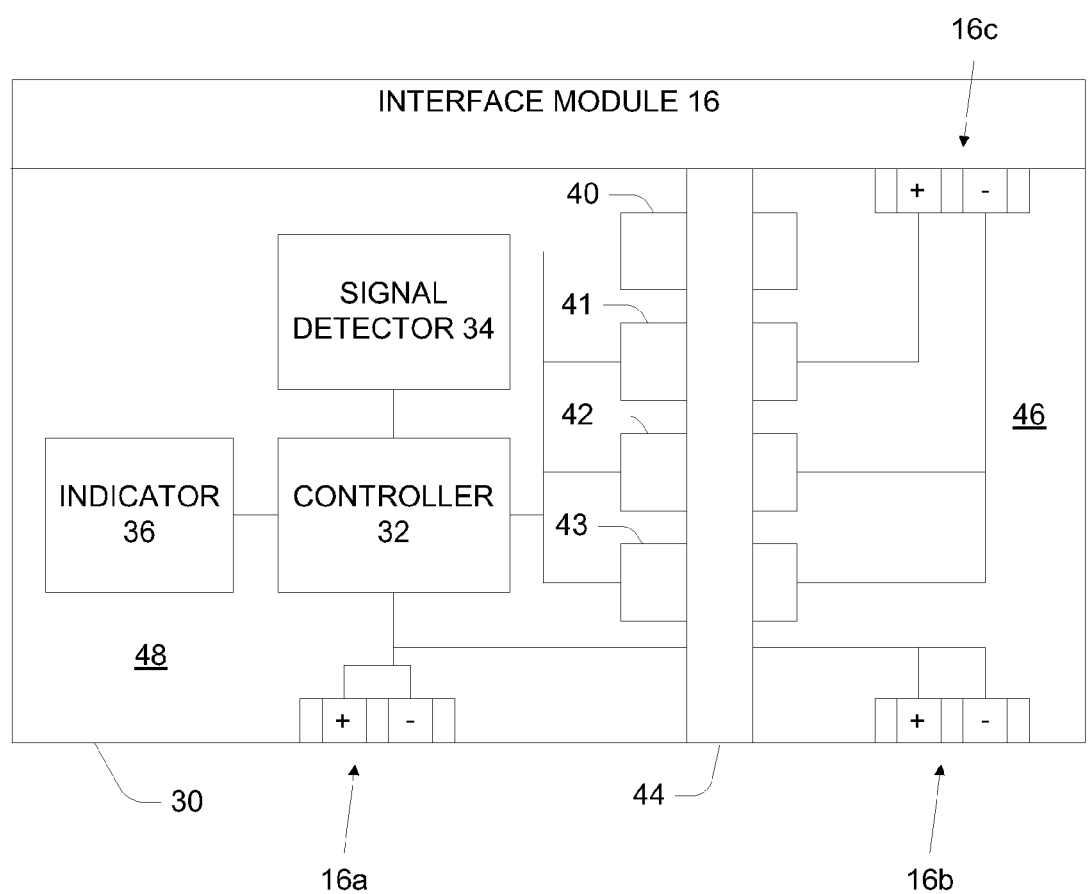
FIG. 2 is a schematic block diagram of components within an interface module for selectively delivering electrical stimulation signals and radio frequency signals to an instrument.

FIG. 2 is a detailed schematic block diagram of interface module 16. Interface module 16 includes a housing 30 that includes a controller 32, a signal detector 34, an indicator 36 and a plurality of relays 40-43. The first input 16a and the second input 16b are both electrically coupled to the controller 32 in order to selectively deliver desired signals to the output 16c. Controller 32 is electrically coupled to signal detector 34, which is configured to detect if an operator wishes to utilize signals from either RF generator 14 or stimulation generator 12, for example based on a signal from selection module 18 (FIG. 1). Moreover, controller 32 is electrically coupled to indicator 36 in order to provide a signal indicative of a particular mode for interface module 16.

Controller 32 is further electrically coupled with the plurality of relays 40-43. In particular, first input 16a includes both a positive and negative contact, selectively coupled to relays 41 and 43, respectively, through controller 32. In a similar manner, second input 16b includes a positive and negative contact, selectively coupled to relays 40 and 42, respectively, through controller 32. Relays 40 and 41 are then coupled with a positive contact of output 16c, while relays 42 and 43 are electrically coupled with a negative contact on output 16c.

Housing 30 further includes an insulating wall 44 (i.e., a firewall), separating the housing 30 into a high voltage chamber 46 (i.e., isolating signals from RF generator 14) and a low voltage chamber 48 (i.e., isolating signals from electrical stimulation generator 12). As such, the high voltage components coupled to RF generator 14 can be electrically isolated from the low voltage components of electrical stimulation generator 12. In one embodiment, wall 44 is formed of polyoxymethylene (POM), for example sold under the DELRIN® tradename, available from the DuPont Corporation of Wilmington, Del. In still a further embodiment, an additional insulating wall can be provided to isolate one or more of the stimulator 12, controller 32, signal detector 34 and indicator 36.

Controller 32, in one example, is embodied as a DS3658 Quad High Current Peripheral Driver available from National Semiconductor Corporation of Santa Clara, Calif. Based on input from signal detector 34, controller 32 will direct either signals from input 16a or signals from input 16b to the plurality of relays 40-43. In one embodiment, relays 40 and 42 are vacuum sealed relays, for example part G47A from Gigavac, LLC of Santa Barbara, Calif. In this embodiment, relays 40 and 42 are Normally Open (NO), also known as contact form A relays. Additionally, relays 41 and 43 can also be vacuum sealed relays, for example part G47B from Gigavac, LLC. In this embodiment, relays 41 and 43 are Normally Closed (NC), also known as contact form B relays.

During operation, signal detector 34 receives a signal from selection module 18 (FIG. 1) to determine whether signals from input 16a or 16b should be sent to output 16c. In one embodiment, absent a signal from selection module 18, signals from input 16a are automatically sent through relays 40 and 42 to output 16c. In this case, the relays 40 and 42 are normally open, so controller 32 can forward signals from input 16a directly to the relays 40 and 42, which in turn are sent to output 16c. Conversely, when a signal is provided to signal detector 34 to use signals from input 16b, controller 32 operates to close relays 40 and 42 and open (e.g., energize) relays 41 and 43. Thus, signals from input 16b pass through relays 41 and 43 to output 16c.

Alternatively, selection module 18 can be configured to provide separate indications to signal detector 34 of whether to pass signals from input 16a through relays 40 and 42 to output 16c or to pass signals from input 16b through relays 41 and 43 to output 16c. Indicator 36 provides an indication of what signals are being directed to output 16c. In one example, one or more light emitting diodes (LEDs) can provide an indication of what signals are directed to output 16c. In this case, one color LED may indicate that interface module 16 is delivering signals from electrical stimulation generator 12 to instrument 10, while another color LED can indicate that interface module 16 is delivering signals from RF generator 14 to instrument 10. In still a further embodiment, other colors/LEDs can indicate other modes, such as a coagulation mode for RF generator 14.

Figure 3:
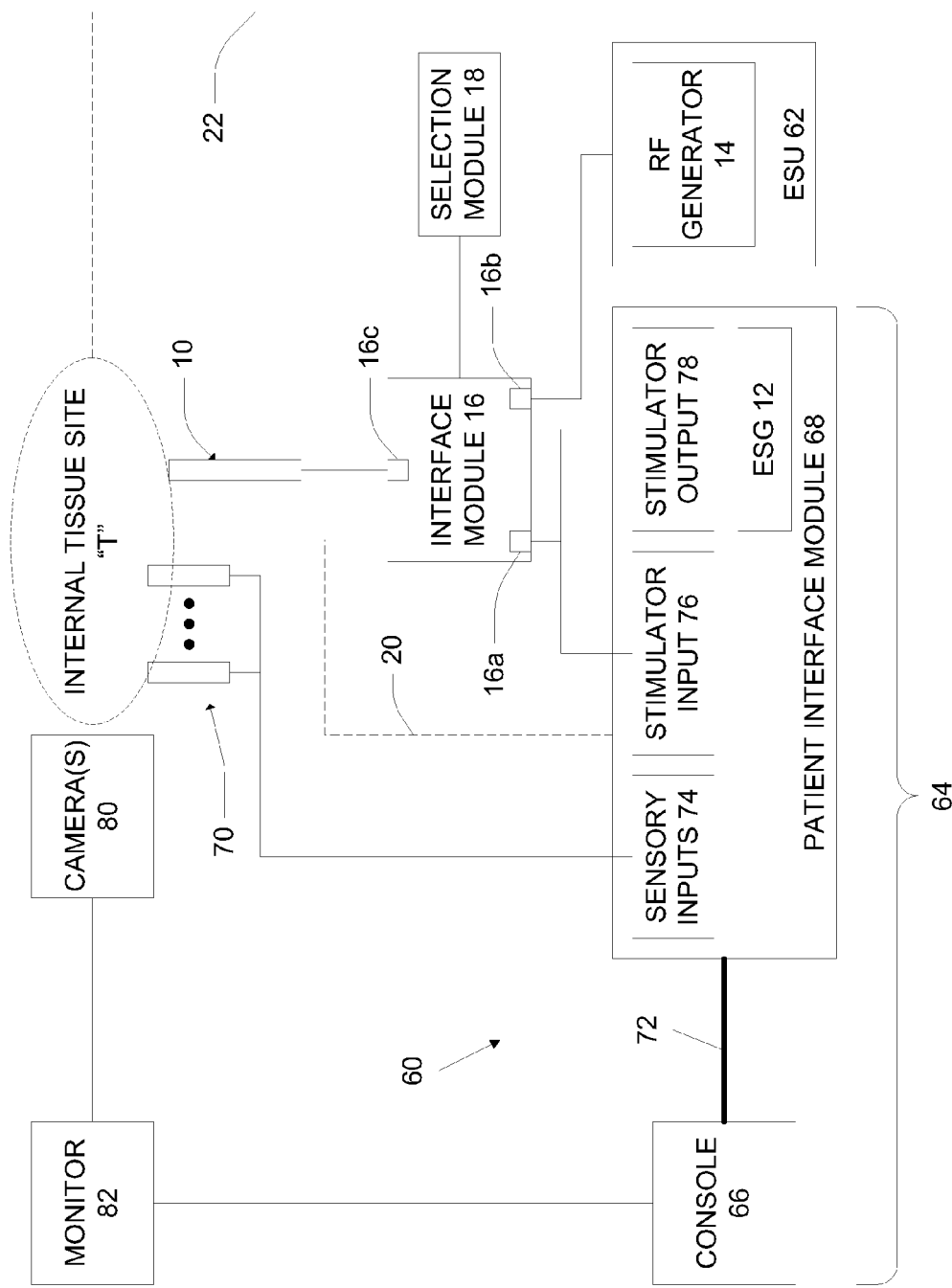
FIG. 3 is a schematic block diagram of a surgical system including an interface module coupled to a nerve integrity monitoring system and an electrosurgical unit.

FIG. 3 is a schematic block diagram of a surgical environment utilizing specific implementations of components illustrated in FIG. 1 to selectively perform nerve monitoring and electrosurgery at an internal target tissue site "T". In one embodiment, the internal target tissue site "T" is accessed laparoscopically and surgery is performed using a surgical robot such as the DaVinci robot available from Intuitive Surgical of Sunnyvale, Calif. In this case, instrument 10 is a wristed instrument coupled to the surgical robot and capable of control by the robot. Electrical stimulation generator 12 is embodied within an evoked potential monitoring system 60 and RF generator 14 is embodied within an electrosurgical unit (ESU) 62. Interface module 16 is coupled to both monitoring system 60 and electrosurgical unit 62 through inputs 16a and 16b as discussed above. Interface module 16 is also coupled to instrument 10 through output 16c. Selection module 18 is operatively coupled to interface module 18 to indicate desired signals to be delivered to instrument 10, so as to selectively complete circuits 20 and 22 (schematically shown).

In general terms, the evoked potential monitoring system 60 is configured to assist in and perform nerve integrity monitoring for virtually any nerve/muscle combination of the human anatomy, as well as recording nerve potential. The system 60 includes a control unit 64, which can assume a wide variety of forms and in one embodiment includes a console 66 and a patient interface module 68. The ESU 62 generates current that is sent to surgical instrument 10 for cutting or otherwise manipulating tissue of a patient.

System 60 includes one or more sensing probes 70, which can be any type of sensing device such as an electrode and can operate to complete circuit 20. In a laporoscopic surgical environment, sensing probes 70 can be coupled to tissue internal to a patient through a suitable introducer such as a cannula, trocar, etc. The control unit 64 facilitates stimulation of the instrument 10, as well as processes all information generated by instrument 10, sensing probes 70 and other components (not shown) during use. The instrument 10 and the control unit 64 are adapted to allow control and variation of a stimulus energy delivered to, and thus a stimulus level delivered by, the instrument 10. Further, the control unit 64 processes information (e.g., patient response) received from instrument 10 and/or sensing probes 70 resulting from delivered stimulation.

Using the sensing probes 70, the system 60 performs monitoring based upon recorded EP activity in response to an electrical current energy delivered by the instrument 10 and/or physical manipulation of tissue. With the one embodiment of FIG. 2, the console 66 and the patient interface module 68 are provided as separate components, communicatively coupled by a cable 72. Alternatively, a wireless link can be employed. Further, the console 66 and the patient interface module 68 can be provided as a single device. In basic terms, however, the patient interface module 68 serves to promote easy connection of stimulus/sensory components (such as the instrument 10 and sensing probes 70), as well as to manage incoming and outgoing electrical signals. The console 66, in turn, interprets incoming signals (e.g., impulses sensed by sensing probes 70), displays information desired by a user, provides audible feedback of signals, presents a user interface (such as by including, for example, a touch screen), and delivers a stimulation energy to the instrument 10 pursuant to control signals from the instrument 10 (via connection to the patient interface module 68, as well as other tasks as desired.

As previously described, the patient interface module 68 communicates with the console 66 through the cable 72 information to and from the instrument 10, as well as information from the sensing probes 70. In effect, the patient interface module 68 serves to connect the patient (e.g., at tissue site "T") to the console 66. To this end, and in one embodiment, the patient interface module 68 includes one or more (preferably eight) sensory inputs 74, such as pairs of electrode inputs electrically coupled to receive signals from the sensing probes 70 (referenced generally in FIG. 3). In addition, the patient interface module 68 provides a stimulator input port 76 (referenced generally in FIG. 3) and a stimulator output port 78 (referenced generally in FIG. 3). The stimulator input port 76 receives control signals from the instrument 10 relating to desired stimulation levels and/or other activities, whereas the stimulator output port 78 facilitates delivery of stimulation energy from the electrical stimulation generator 12 to the instrument 10. The patient interface module 68 can further provide additional component port(s), such as a ground (or return electrode) jack, auxiliary ports for additional stimulator probe assemblies, etc.

The sensing probes 70 are coupled to the patient (e.g., selected tissue) to provide signals to the patient interface module 68. In one embodiment, the plurality of probes 70 includes eight probes that are electronically coupled to sensory inputs 74. In normal operation, the probes 70 sense electrical signals from the patient and send the signals to patient interface module 68. These signals include an electrical impulse from patient tissue, which is indicative of EP activity (e.g., a bio-electric response) in the patient. Upon sensing that instrument 10 is proximate and/or contacting a nerve so as to create EP activity (e.g., as a result of signals from ESG 12 and/or ESU 62), sensing probes 70 can provide an indication to interface module 16 that will disable any further signals from ESU 62 being transmitted to tissue site "T" through instrument 10. As a result, damage to nerves in tissue site "T" can be prevented by automatically disabling operation of ESU 62 (e.g., by suppressing its signals). In a further embodiment, interface module 16 can further provide an alert (e.g., an audible and/or visual signal) that sensing probes 70 are sensing EP activity.

ESU 62 can be configured to perform various electrosurgical modalities such as monopolar, bipolar and/or combinations thereof. Moreover, ESU 62 can be configured to deliver different types of RF signals so as to achieve a desired tissue effect. To this end, various waveforms and/or power settings can be applied to instrument 10 through interface module 16 as desired. Additionally, instrument 10 can be equipped with a tip desired for a particular application of signals from ESU 62.

In a further embodiment, one or more cameras 80 are positioned so as to provide visual information of the surgical site to assist the surgeon in performing the desired surgical procedure. The one or more cameras 80 can also be introduced to site "T" laparoscopically. Video data from the one or more cameras 80 can be provided to a monitor 82, along with data from console 66. To this end, the surgeon is provided with both visual information of the surgical site as well as visual information indicative of recorded responses from sensing probes 70 and/or instrument 10. By selectively providing stimulation signals and RF signals, the surgeon, through use of monitor 82, can visually check whether a targeted site is a nerve or whether RF signals can be sent so as to cut the targeted tissue. As such, a surgeon can quickly discern and cut targeted tissue.

Although the present disclosure has been described with reference to preferred embodiments, workers skilled in the art will recognize that changes can be made in form and detail without departing from the spirit and scope of the present disclosure.

What is claimed is:

1. An interface module for simultaneous use with an electrical stimulation generator and an electrosurgical unit, the interface module comprising:
   a first input configured to receive electrical stimulation signals for evoked potential monitoring for locating a nerve, from the electrical stimulation generator;
   a first set of relays coupled to the first input;
   a second input apart from the first input and configured to receive radio frequency signals from an RF generator of the electrosurgical unit;
   a second set of relays coupled to the second input;
   wherein the interface module is configured such that the first input and second inputs simultaneously receive the electrical stimulation signals and the radio frequency signals, respectively, the electrical stimulation signals differing from the radio frequency signals;
   an output configured to deliver output signals to a single instrument and coupled to the first set of relays and the second set of relays;
   a signal detector configured to receive an indication to deliver only one of the electrical stimulation signals and the radio frequency signals as the output signals at a time; and
   a controller coupled to the first input, the second input, the signal detector, the first set of relays and the second set of relays, the controller configured to selectively energize the first set of relays and the second set of relays based on the indication from the signal detector so as to deliver the corresponding electrical stimulation signals or radio frequency signals to the output.

2. The interface module of claim 1 wherein the signal detector receives the indication from a selection module.

3. The interface module of claim 2 wherein the selection module is one of a mechanical switch and an electrical switch.

4. The interface module of claim 1, wherein the first set of relays and the second set of relays are vacuum sealed.

5. The interface module of claim 1, further comprising a housing maintaining the controller, the signal controller, and the inputs, the housing further including an insulating wall separating the first input and the second input.

6. The interface module of claim 5, wherein the insulating wall is formed of polyoxymethylene.

7. The interface module of claim 1, further comprising an indicator providing a visual reference of the indication.

8. The interface module of claim 1 wherein the radio frequency signals are configured for coagulation of tissue.

9. The interface module of claim 1 wherein the radio frequency signals are configured for cutting of tissue.

10. The interface module of claim 1, wherein the first input includes a first input positive contact and a first input negative contact, and further wherein a first relay of the first set of relays is coupled to the first input positive contact, and a second relay of the first set of relays is coupled to the first input negative contact.

11. The interface module of claim 10, wherein the output includes an output positive contact and an output negative contact, and further wherein the first relay is coupled to the output positive contact and the second relay is coupled to the output negative contact.

12. The interface module of claim 10, wherein the second input includes a second input positive contact and a second input negative contact, and further wherein a first relay of the second set of relays is coupled to the second input positive contact, and a second relay of the second set of relays is coupled to the second input negative contact.

13. The interface module of claim 12, wherein the output includes an output positive contact and an output negative contact, and further wherein the first relay of the first set of relays and the first relay of the second set of relays are coupled to the output positive contact, and the second relay of the first set of relays and the second relay of the second set of relays are coupled to the output negative contact.

* * * * *